United States Patent

Fujita et al.

[11] 3,978,100
[45] Aug. 31, 1976

[54] ALLENIC ESTERS, PROCESS FOR PREPARATION THEREOF AND PROCESS FOR REARRANGEMENT THEREOF

[75] Inventors: Yoshiji Fujita, Kurashiki; Yoshiaki Omura, Okayama; Takashi Hishida; Kazuo Itoi, both of Kurashiki, all of Japan

[73] Assignee: Kuraray Co., Ltd., Kurashiki, Japan

[22] Filed: Apr. 18, 1974

[21] Appl. No.: 461,977

[30] Foreign Application Priority Data
Apr. 18, 1973 Japan............................ 48-44308
May 15, 1973 Japan............................ 48-54334
May 15, 1973 Japan............................ 48-54335

[52] U.S. Cl. ............ 260/410.9 R; 260/486 R; 260/468 R; 260/468 H
[51] Int. Cl.² .......................................... C11C 3/02
[58] Field of Search ......... 260/DIG. 44, 410.9 R, 260/486 R, 468 H, 468 R

[56] References Cited
UNITED STATES PATENTS

| | | |
|---|---|---|
| 3,236,869 | 2/1966 | Thompson ............ 260/410.9 R |
| 3,716,565 | 2/1973 | Henrick ............... 260/410.9 R |
| 3,732,282 | 5/1973 | Henrick ............... 260/410.9 R |
| 3,737,442 | 6/1973 | Baum .................. 260/410.9 R |
| 3,755,411 | 8/1973 | Henrick ............... 260/410.9 R |

*Primary Examiner*—Patrick P. Garvin
*Assistant Examiner*—John F. Niebling
*Attorney, Agent, or Firm*—Bacon & Thomas

[57] ABSTRACT

Allenic esters of the formula:

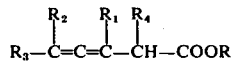

(specific examples of R, $R_1$, $R_2$, $R_3$ and $R_4$ are given) and a process for the preparation thereof which comprises reacting propargyl alcohol derivatives with 2-substituted ortho-acetic acid esters in the presence of an acidic catalyst. These allenic esters are rearranged in the presence of an alkali catalyst to form $\alpha$, $\beta$, $\gamma$, $\delta$-unsaturated carboxylic acid esters and are useful as intermediates in the synthesis of various perfumes, medicines, agricultural chemicals and the like.

7 Claims, No Drawings

ALLENIC ESTERS, PROCESS FOR PREPARATION THEREOF AND PROCESS FOR REARRANGEMENT THEREOF

BACKGROUND OF THE INVENTION

1. Field of the Invention

This invention relates to allenic acid esters and to a process for the preparation thereof and further to a process for preparing $\alpha,\beta,\gamma,\delta$-unsaturated carboxylic acid esters by rearranging allenic acid esters.

2. Description of the Prior Art

Allenic acid esters are known and are useful as intermediates in the preparation of various types of perfumes, pharmaceuticals, agricultural compounds and the like. For example, U.S. Pat. No. 3,737,452 discloses allenic esters of the formula:

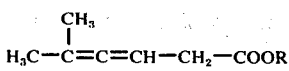

wherein "R" in formula (I) is a primary or secondary lower alkyl of 1 to 6 carbon atoms. These compounds are prepared by reacting 3-methyl-1-butyn-3-ol with an orthoester and may be rearranged to yield the corresponding lower alkyl 5-methylhexa-2,4-dienoate in the presence of a base.

SUMMARY OF THE INVENTION

In accordance with the invention, novel allenic esters are provided which are represented by the following formula (II):

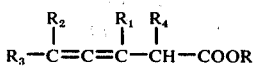

wherein $R_1$, $R_2$, and $R_4$ each represents hydrogen or a hydrocarbon radical such as an alkyl, cycloalkyl, aryl, alkenyl, cycloalkenyl, alkynyl or aralkyl group, which may contain a non-interfering substituent such as a halogen atom or an alkoxy, acyl or acyloxy group and which may be interrupted by a hetero-atom such as O, N or S or a functional group such as —CO— or —CONH—; $R_2$ and $R_3$ may together form a cyclic ring; $R_3$ represents a hydrocarbon radical having at least 2 carbon atoms including the hydrocarbon groups identified above for $R_1$, $R_2$ and $R_4$; and R represents a hydrocarbon radical having from 1 to 8 carbon atoms.

Also in accordance with the invention, a process is provided for preparing the allenic esters of the above formula (II) comprising reacting a propargyl alcohol compound of the formula (III):

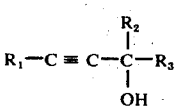

with a 2-substituted ortho-acetic acid ester of the formula (IV):

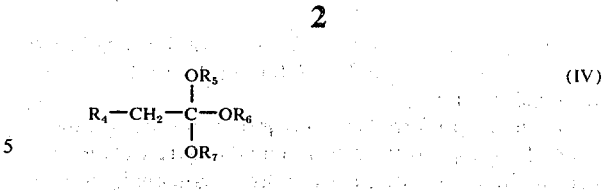

wherein $R_1$, $R_2$, $R_3$ and $R_4$ are as defined above and $R_5$, $R_6$ and $R_7$, which may be the same or different, each has the same meaning as R in the formula (II).

Further in accordance with the invention, a process is provided for preparing an $\alpha,\beta,\gamma,\delta$-unsaturated carboxylic acid ester of the formula (V):

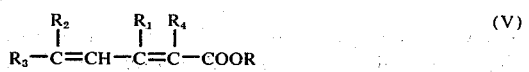

by rearranging the allenic ester of formula (II) in the presence of a basic catalyst.

DESCRIPTION OF THE PREFERRED EMBODIMENTS

In formula (II), $R_1$, $R_2$ and $R_4$ are each selected from the group consisting of a hydrogen atom, an alkyl group of 1 to 20 carbon atoms, a cycloalkyl group of 6 to 20 carbon atoms, an aryl group of 6 to 20 carbon atoms, an alkenyl group of 2 to 20 carbon atoms, a cycloalkenyl group of 6 to 20 carbon atoms, an alkynyl group of 2 to 20 carbon atoms and an aralkyl group of 7 to 20 carbon atoms.

Typical alkyl groups include methyl, ethyl, propyl, butyl, amyl, hexyl, heptyl, octyl, nonyl, decyl, undecyl, dodecyl, pentadecyl, hexadecyl, eicosyl, pentacosyl, triacontyl, etc.

Typical cycloalkyl groups include cyclobutyl, cyclopentyl, cyclohexyl, etc.

Exemplary aryl groups include phenyl, naphthyl, etc.

Typical alkenyl groups are vinyl, allyl, pentenyl, 1-butenyl, etc.

Exemplary cycloalkenyl groups include 1-cyclohexenyl, 1-cyclopentenyl, etc.

Typical alkynyl groups include ethynyl, propynyl, 1-butynyl, 1-pentynyl, 1-hexynyl, etc.

Exemplary aralkyl groups include benzyl, methyl phenyl, ethyl phenyl, propyl phenyl, dimethyl phenyl, ethyl-methyl phenyl, etc.

Each of the alkyl, cycloalkyl, aryl, alkenyl, cycloalkenyl, alkynyl and aralkyl groups may be unsubstituted or substituted by any non-interfering substituent such as a halogen atom (e.g., chlorine, fluorine, iodine, etc.), and alkoxy group (e.g., methoxy, ethoxy, propoxy, butoxy, etc.), an acyl group, an acyloxy group, etc. Thus, typical substituted groups for $R_1$, $R_2$, $R_3$ and $R_4$ are 2.6-dimethyl-6-ethoxy-heptenyl group (Product: 3.7.11-trimethyl-11-ethoxy-2.4-dodecanoate) or 2.6-dimethyl-6-chloro heptenyl group (Product: 3.7.11-trimethyl-11-chloro-2.4-dodecanoate).

Similarly, each of these groups may contain a heteroatom such as O, N or S, etc., and examples of typical groups are 2.2.6-trimethyl-4.5-episulfide-heptyl group (Product: 3.7.11-trimethyl-9.10-episulfide-2.4-dodecanoate) or 1-ethoxy-2.2.6-trimethyl-5-cyclohexanone-1-yl-group (Product: Ethyl 5-(1-ethoxy-2.2.6-trimethyl-5-cyclohexanone-1-yl)-3-methyl-2.4-pentadienoate).

Further, these hydrocarbon groups may contain functional groups such as —CO—, —CONH, etc., and typical examples are 2.2.6-trimethyl-4-oxy-heptyl group (Product: 3.7.7.11-tetramethyl 9-oxy-2.4-dodecadienoate)

The most preferred allenic esters are those where each of $R_1$, $R_2$ and $R_4$ in formula (II) represents hydrogen or the above-identified hydrocarbon radicals having only from 1 to 8 carbon atoms, and where $R_3$ represents the group $R'-A_m-$ in which $R'$ is a hydrocarbon radical of 5 to 30 carbon atoms having the structure

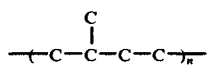

where $n$ is an integer of 1 to 6, $-A-$ is an alkylene, alkenyl or alkynylene radical having 1 to 3 carbon atoms, and $m$ is an integer of 0 or 1. In this case, the hydrocarbon radicals of $R_1$, $R_2$ and $R_4$ and the group $R'-A_m-$ may also include non-interfering substituents, hetero-atoms and functional groups such as those as mentioned above.

Although it is the intention to include within the scope of the invention all allenic esters within the definition of formula (II), the esters of the following acids are given for purposes of illustration:

3,4-heptadienoic acid
5-cyclohexyl-3,4-pentadienoic acid
5,9-dimethyl-3,4,8-decatrienoic acid
2,5,9-trimethyl-3,4,9-decatrienoic acid
5,9,13-trimethyl-3,4,8,12-pentadecatetraenoic acid
5-methyl-3-phenyl-3,4-hexadienoic acid
3,4-pentadienoic acid
3-methyl-3,4-pentadienoic acid
3,7,11-trimethyl-11-ethoxy-3,4-dodecadienoic acid
5-(2,6,6-trimethyl-1-cyclohexenyl)-3-methyl-3,4-pentadienoic acid
3.7.11-trimethyl-11-chloro-3.4-dodeca dienoic acid
3.7.11-trimethyl-9.10-episulfide-3.4-dodecadienoic acid
3.7.7.11-tetramethyl-9-oxy-3.4-dodecadienoic acid and
5-(1-ethoxy-2.2.6-trimethyl-5-cyclo hexanone-1-yl)-3-methyl-3.4-pentadienoic acid In formula (II) R is a hydrocarbon radical of 1 to 8 carbon atoms, including alkyl (e.g., methyl, ethyl, propyl, butyl, amyl, hexyl, heptyl, octyl, etc., and variations thereof), cycloalkyl (e.g., cyclobutyl, cyclohexyl, etc.), aryl (e.g., phenyl, etc.) alkenyl (e.g., vinyl, allyl, pentenyl, hexenyl, etc.), cycloalkenyl (e.g., cyclohexenyl, cyclobutenyl, etc.), alkynyl (e.g., ethynyl, propynyl, hexynyl, etc.) and aralkyl (e.g., benzyl, methyl phenyl, ethyl phenyl, dimethyl phenyl, etc.). It is the intention, however, to include all "hydrocarbon" groups having from 1 to 8 carbon atoms within the scope of R.

The allenic esters represented by the above formula (II) may be easily prepared in high yields by the method of the invention. The reaction proceeds substantially quantitatively and the yields exceeds 90% in many cases.

More specifically, in accordance with this invention, the allenic esters represented by the above formula(II) are prepared by reacting, in the presence of an acidic catalyst, a propargyl alcohol derivative represented by the following formula (VI):

wherein $R_1$, $R_2$ and $R_3$ are as defined above with respect to formula (II) with a 2-substituted ortho-acetic acid ester represented by the following formula (VII):

wherein $R_4$ is as defined above with respect to formula (II), and $R_5$, $R_6$ and $R_7$, which may be the same or different, have the same meaning as R in the above formula (II).

Typical examples of the compound of the above formula (VI) are 2-hexyn-1-ol, 2-octyn-1-ol, 1-pentyn-3-ol, 1-hexyn-3-ol, 5-methyl-1-hexyn-3-ol, 3-methyl-1-pentyn-3-ol, 3-ethyl-7-methyl-1-decyn-6-en-3-ol, dehydrolinalool (i.e., 3,7-dimethyl-1-octyn-6-en-3-ol) dehydronerolidol (i.e., 3,7,11-trimethyl-3,10-dodecadien-1-yn-3-ol), 3,7,11,15-tetramethyl-6,10,14-hexadecatrien-1-yn-3-ol, 3,7-dimethyl-1-octyn-3ol, 3,7,11,15-tetramethyl-6,10,14-hexadecatrien-1-yn-3-ol, 3,7,11,15-tetramethyl-1-hexadecyn-3-ol, cyclohexylethynylcarbinol, 3-methyl-1,5-hexadyn-1-ol, etc.

As the compound of the general formula (IV), there can be mentioned, for example, 1,1,1-trimethoxyethane, 1,1,1-triethoxyethane (i.e., ethyl ortho-acetate), 1,1,1-triethoxypropane, 1,1,1-triethoxybutane, 3-methyl-1,1,1-trimethoxybutane, 3,7-dimethyl-1,1,1-triethoxyoctane, 2-phenyl-1,1,1-triehoxyethane, 2-(o-methylphenyl)-1,1,1-triethoxyethane, 2-(m-methylphenyl)-1,1,1-triethoxyethane, 2-cyclohexyl-1,1,1-trimethoxyethane, 1,1-dimethoxy-1-pentoxyethane, etc. Among these compounds, ethyl ortho-acetate is the most easily available commercially and is preferred.

It is the intention to include within the scope of the invention all compounds falling within the broad definition of formulas (III) and (IV) above, it being understood by those skilled in the art that the above exemplary compounds of formulas (III) and (IV) are for purposes of illustration only.

The use of a catalytic amount of an acidic catalyst is preferred in the process of the invention, with any conventional weak acid catalyst being operable. Typical examples are carboxylic acids such as acetic acid, propionic acid, butyric acid, isobutyric acid, n-valeric acid, malonic acid, succinic acid and adipic acid; sulfonic acids such as benzene-sulfonic acid and p-toluene-sulfonic acid; phenols such as phenol, o,m,p-nitrophenols, o,m,p-cresols, o,m,p-xylenols, 2,6-dimethyl phenol, 2,6-di-t-butyl phenol, 2,4,6-tri-sec-butyl phenol, 2,4,6-tri-t-butyl phenol, 4-methyl-2,6-di-t-butyl phenol, 4-methyl-3,5-di-t-butyl phenol, hydroquinone, 2,5-di-t-butyl hydroquinone; mineral acids such as boric acid, phosphoric acid, hydrochloric acid and sulfuric acid; and Lewis acids such as zinc chloride, iron chloride and boron trifluoride.

The catalyst is preferably used in an amount of from 0.1 to 20% by weight, most preferably from 1 to 10% by weight, based on the weight of the propargyl alcohol derivative (III).

The use of a solvent is not particularly essential and although the process may be performed in the absence of a solvent, it is preferred that organic solvents having a boiling point of 80 to 150°C. be employed, such as n-heptane, n-octane, toluene and o-, m- or p-xylene. It is also possible to employ the starting 2-substituted ortho-acetate as the reaction solvent by employing the same in an amount which is in excess over the amount of the propargyl alcohol derivative.

The reaction may be conducted at a temperature within the range of from 50° to 200°C., but in view of the reaction rate and selectivity, it is preferred that the reaction be carried out at a temperature of from 100° to 150°C.

The propargyl derivative (III) and the ester (IV) should preferably be employed in about equimolar amounts, although the molar ratio of (III) to (IV) may vary from 1.0:1.1 to 1:4.

Since the reaction is an equilibrium reaction, at the termination of the reaction there is obtained an equilibrium composition of a propargyl alcohol derivative, an allenic ester and an intermediate ester-exchange product. Where the reaction is conducted while expelling the alcohol formed as a by-product, such as ethanol, the intended product can be obtained sustantially quantitatively. However, if it is disadvantageous to distill the reaction mixture to remove the alcohol, it is preferred that the reaction be stopped at an appropriate point an the by-product alcohol be removed from the reaction mixture by any appropriate technique.

When the allenic ester of the invention is maintained in the presence of an alkali catalyst, a rearrangement reaction readily occurs, resulting in the formation of an $\alpha,\beta,\gamma,\delta$-unsaturated carboxylic acid ester represented by the following formula (VIII):

wherein R1, $R_2$, $R_3$, $R_4$ and R are as defined above in formula (II).

Any mild base can be employed as the alkali catalyst in the rearrangement reaction of the invention. Typical bases include alkalis such as the hydroxides, oxides and carbonates of the metals of Groups I and II of the Periodic Table, and nitrogen-containing organic bases, e.g., pyridine and N-methylpyrrolidone. Preferred examples of the alkali catalyst are sodium hydroxide, potassium hydroxide, barium hydroxide and the like. The alkali catalyst can be used in an amount of at least 0.1% by weight based on the weight of the allenic ester, but it is generally preferred that the alkali catalyst be used in an amount of from 1 to 5% by weight, based on the weight of the allenic ester.

While the rearrangement may be conducted in the absence of a solvent, it is preferred that a mixture of a lower alcohol (such as methanol, ethanol or propanol) with a small amount of water be used as the reaction solvent.

The rearrangement reaction can be conducted at a temperature of 0° to 150°C. The reaction proceeds sufficiently at room temperature, and it is preferred that the reaction be carried out at a temperature approximating room temperature.

The resulting $\alpha,\beta,\gamma,\delta$-unsaturated carboxylic acid ester is valuable as in intermediate for the synthesis of various perfumes, medicines, agricultural chemicals and the like.

This $\alpha,\beta,\gamma,\delta$-unsaturated carboxylic acid ester can also be prepared by forming an allenic ester by reacting the above-mentioned propargyl alcohol derivative and 2-substituted orthoacetic acid ester, adding an alkali catlayst to the resulting allenic ester-containing reaction mixture without separation of the allenic ester, and rearranging the allenic ester contained in the mixture.

The unsaturated carboxylic acid ester may be readily ester-exchanged with other alcohols to form other esters.

The prior art has suggested the following processes for the synthesis of the $\alpha,\beta,\gamma,\delta$-unsaturated carboxylic acid esters represented by the above formula (VIII):

1. subjecting a ketone or aldehyde represented by the following general formula (IX):

wherein $R_1$, $R_2$ and $R_3$ are as defined in above formula (II), and a compound represented by the following formula (X):

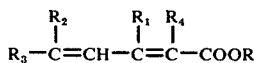

wherein $R_4$ and R are as defined in formula (II) and X repesents a halogen atom, to the Wittig reaction or the Reformatsky reaction.

2. subjecting a ketone or aldehyde represented by the above formula (IX) and an active methylene-containing compound such as malonyl(ethyl) cyanoacetate to the Knoevenagel reaction.

Each of these known processes requires complicated reaction operations and the yield of the intended unsaturated carboxylic acid ester is low.

According to the process of the invention, the intended $\alpha,\beta,\gamma,\delta$-unsaturated carboxylic acid ester can be prepared in a high yield by one step (or two steps) from a compound of the formula (VI) which is a starting compound of the ketone or aldehyde of the formula (IX).

As stated hereinabove, the allenic esters of the invention can be used as an intermediate for synthesis of various compounds.

For instance, a 5,9,13-trimethyl-3,4,8,12-pentadecatetraenoate of the following formula (XI), one of the allenic esters of this invention,

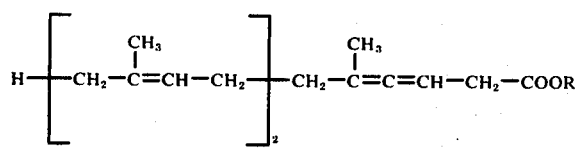
(XI)

gives a farnesylideneacetic acid ester of the following formula (XII)

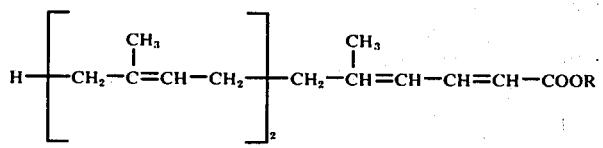
(XII)

in the presence of an alkali catalyst. This $\alpha,\beta,\gamma,\delta$-unsaturated carboxylic acid ester is readily hydrogenated to a farnesylacetic acid ester of the following formula (XIII)

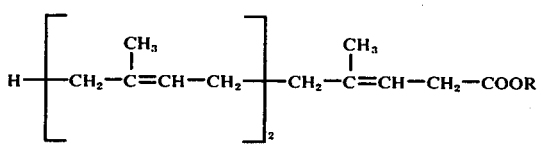
(XIII)

The so-obtained ester, especially the geraniol ester, has an anti-ulcer activity, as disclosed in U.S. Pat. No. 3,154,570.

As another example of the utility of the allenic esters of the invention, a 3,7,11-trimethyl-11-ethoxy-3,4-dodecadienoate of the following formula (XIV)

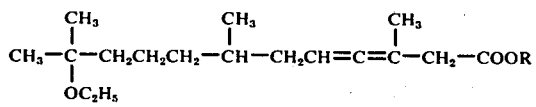
(XIV)

can readily be prepared from 6,10-dimethyl-10-ethoxyundecan-2-yn-4-ol of the following formula (XV)

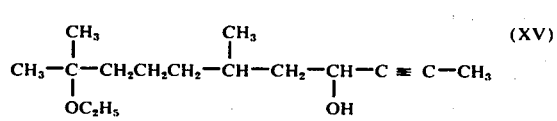
(XV)

and an ortho-acetic acid ester. When this allenic ester (XIV) is rearranged with the use of an alkali catalyst, there is obtained a 3,7,11-trimethyl-11-ethoxy-2,4-tridecadienoate of the following formula (XVI)

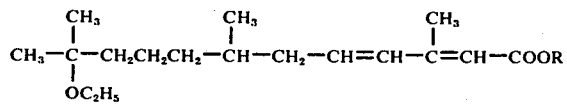
(XVI)

The resulting ester (XVI), especially the ethyl ester, is useful as a juvenile hormone.

When 4-(2,6,6-trimethyl-1-cyclohexenyl)-4-hydroxy-butyn-2 of the following formula (XVII)

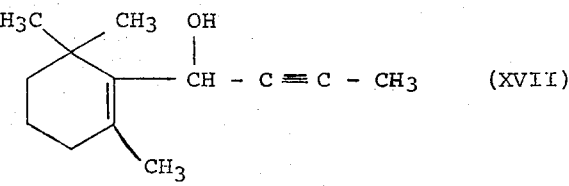
(XVII)

is reacted with an ortho-acetic ester, there is obtained a 5-(2,6,6-trimethyl-1-cyclohexenyl)-3-methyl-3,4-pentadienoate of the following formula (XVIII)

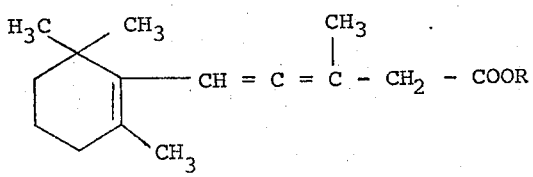

(XVIII)

This allenic ester (XVIII) is readily rearranged in the presence of an alkali catalyst to form a 5-(2,6,6-trimethyl-1-cyclohexenyl-3-methyl-2,4-pentadienoate of the following formula (XIX)

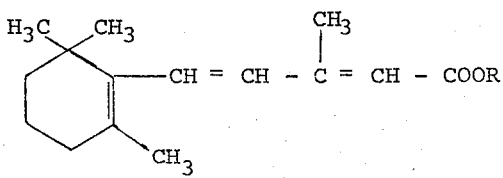

(XIX)

This α,β,γ,δ-unsaturated carboxylic acid ester (XIX) can be used as an intermediate in the synthesis of abscinic acid which is useful as a plant growth regulator.

The following examples are intended to illustrate the invention as applied to representative allenic esters and processes for preparing and rearranging the same. Further, the following examples are for the purpose of illustrating the best mode contemplated for carrying out the invention and to supplement the foregoing disclosure of the invention with additional descriptions of the manner and process of carrying out the invention so as further to enable those skilled in the art to do so.

EXAMPLE 1

A 200 ml- capacity three-necked flask was charged with 78 g of ethyl ortho-acetate, 20 g of 1-pentyn-3-ol and 2.0 g of butyric acid and was heated at 117° to 122°C. and ethanol formed as a by-product was distilled off. Even after completion of the distillation of the ethanol, the mixture was agitated at the above temperature for several hours. After complete extinction of the starting alcohol was confirmed by the gas chromatography, the reaction mixture was subjected to distillation under reduced pressure, and a fraction boiling at 87° to 89.5°C. under 16 mm Hg was collected. The intended ethyl 3,4-heptadienoate was obtained in a yield of 97%.

EXAMPLE 2

A mixture of 66 g of ethyl ortho-acetate, 25 g of cyclohexylethynylcarbinol and 2.5 g of propionic acid was agitated at 130 to 135°C. for 8 hours while distilling off ethanol. The resulting liquid mixture was directly subjected to distillation under reduced pressure and a fraction boiling at 107° to 108°C. under 5 mm Hg was collected. Ethyl 5-cyclohexyl-3,4-pentadienoate was obtained in a yield of 93%.

EXAMPLE 3

A mixture of 65.6 g of ethyl ortho-acetate, 30.4 g of dehydrolinalool and 1.5 g of isobutyric acid was reacted at 130° to 140°C. for 8 hours. Distillation was conducted after the reaction in the same manner as in the preceeding Examples, and a fraction boiling at 92 to 94°C. under 0.5 mm Hg was collected. Ethyl 5,9-dimethyl-3,4,8-decatrienoate was obtained in a yield of 96%.

EXAMPLE 4

In the same manner as in the preceeding Examples, 50 g of ethyl ortho-propionate, 21.6 g of dehydrolinalool and 2.1 g of isobutyric acid were reacted at 135° to 140°C. for 4 hours and the resulting reaction mixture was subjected to distillation under reduced pressure. Ethyl 2,5,9-trimethyl-3,4,8-decatrienoate was obtained in a yield of 98.5% from a fraction boiling at 129 to 130°C. under 2.3 mm Hg.

EXAMPLE 5

In the same manner as in the preceeding Examples, 32.4 g of ethyl ortho-acetate, 22 g of dehydronerolidol and 1.5 g of propionic acid were reacted at 135 to 140°C. for 6 hours and the resulting reaction mixture was subjected to distillation under reduced pressure. Ethyl 5,9,13-trimethyl-3,4,8,12-pentadecatetraenoate was obtained in a yield of 96% from a fraction boiling at 144 to 146°C. under 0.025 mm Hg.

EXAMPLE 6

20 g of the ethyl 3,4-heptadienoate obtained in Example 1 was agitated at 40°C. for 2 hours in 80 ml of propanol in the presence of 3 ml of 4N KOH as a catalyst. The resulting reaction mixture was neutralized with 4N HCl, dried and distilled. Ethyl 2,4-heptadienoate was obtained in a yield of 92% from a fraction boiling at 64.5°C. under 2.5 mm Hg. The double bond at the 2-position was of the trans-form and the double bond at the 4-position was composed of 55% of the cis-form and 45% of the trans-form.

EXAMPLE 7

25 g of the ethyl 2,5,9-trimethyl-3,4-decatrienoate obtained in Example 4 was agitated at room temperature for 2 hours in 80 ml of ethanol in the presence of 0.5 g of KOH as a catalyst, and the resulting reaction mixture was neutralized with 4N HCl, dried and subjected to distillation under reduced pressure. Ethyl 2,5,9-trimethyl 12,4,8-decatrienoate was obtained in a yield of 92% from a fraction boiling at 137.5° to 138.5°C. under 0.7 mm Hg. The double bond at the 2-position was of the trans-form and in the double bond at the 4-position, the cis: trans ratio was 55:45.

EXAMPLE 8

20 g of ethyl 5,9,13-trimethyl 3,4,8,12-pentadecatetraenoate was reacted at room temperature for 2 hours in 80 ml of ethanol in the presence of 5 ml of 4N KOH, and the resulting reaction mixture was neutralized and subjected to distillation under reduced pressure. Ethyl farnesylideneacetate was obtained in a yield of 91% from a fraction boiling at 174° to 175°C. under 0.04 mm Hg.

EXAMPLE 9

20 g of ethyl 5,9,13-trimethyl-3,4-tetradecadienoate and 1 g of potassium carbonate were heated at 40° to 45°C. for 3 hours in the absence of a solvent to effect the rearrangement reaction. Then, the reaction mixture was neutralized with 4N HCl and subjected to distillation under reduced pressure. Ethyl 5,9,13-trimethyl-2,4-tetradecadienoate was obtained in a yield of 93% from a fraction boiling at 143 to 145°C. under 1 mm Hg.

EXAMPLE 10

Ethyl 4-cyclohexylidene-3-butenoate was reacted at 50°C. for 4 hours in 80 ml of methanol in the presence of 1.5g of calcium carbonate as a catalyst. In the same manner as in the preceding Examples, the resulting reaction mixture was neutralized and subjected to distillation under reduced pressure. Ethyl 4-cyclohexylidene-2-butenoate was obtained in a yield of 92% from a fraction boiling at 111 to 114°C. under 3 mm Hg.

EXAMPLE 11

32.4 g of ethyl ortho-acetate, 22 g of dehydronerolidol and 1.5 g of propionic acid were reacted at 135° to 140°C. for 6 hours. The reaction mixture was cooled to room temperature, and 4N NaOH aqueous solution was added to the reaction mixture to neutralize it and make it alkaline. Then, the reaction was further conducted at room temperature for 2 hours. The reaction mixture was poured into water and extracted with ether. The solvent was removed and the residue was distilled under high vacuum. The fraction boiling at 174 to 175°C. under 0.04 mm Hg was composed of ethyl farnesylideneacetate as in Example 7. The yield was 89%.

EXAMPLE 12

24 g of 10-ethoxy-6,10-dimethyl-undeca-2-yn-4-ol, 24.3 g of ethyl ortho-acetate and 1.2 g of hydroquinone were mixed and reacted at 160°C. for 4 hours while distilling off ethanol (the by-product) from the reaction system. After the reaction, the product was permitted to cool to room temperature and to the cooled product was added 10 ml of a 1 weight percent caustic soda solution dissolved in a mixture of 2 parts by weight water and 98 parts by weight methanol, and the resulting mixture was stirred for 1 hour. The resulting product was neutralized with 1N, HCl, extracted with dimethyl ether, washed with water and dried with magnesium sulfate. After separating the reaction solvent and distilling the residue under vacuum, 28.4 g of a yellowish liquid was obtained in a yield of 091%, which was confirmed as ethyl-11-ethoxy-3,7,11-trimethyl-2,4-dodecadienoate, by reason of the fact that the holding time of a gas-chromatographic analysis, the absorption spectrum of an IR analysis and the spectrum of a N.M.R. analysis were in accord with those of a standard which was produced by a reaction between ethyl-γ-bromosenecionate (i.e., ethyl-4-bromo-3-methyl crotonate) and ethoxy citronellal by the Wittig reaction.

EXAMPLE 13

23 g of ethyl 5,9,13-trimethyl-3,4,8,12-pentadecatetraenoate obtained according to the method of Example 5 and 23.1 g of geraniol were added to 50 ml of xylene, and the reaction was carried out under reflux for 10 hours in the presence of 0.57 g of KOH as a catalyst while expelling ethanol formed as a byproduct to obtain geranyl farnesylideneacetate in a yield of 81%.

EXAMPLE 14

14.5 g of ethyl farnesylideneacetate obtained according to the method of Example 10 and 23.1 g of geraniol were added to 50 ml of xylene, and the reaction was carried out under reflux for 10 hours in the presence of 0.57 g of KOH as a catalyst while removing ethanol formed as a by-product. The resulting reaction mixture was neutralized and subjected to distillation under reduced pressure. The fraction boiling at 198 to 201°C. under 0.03 mm Hg was composed of geranyl farnesylideneacetate. The yield was 84.5%.

What is claimed is:

1. A process for the preparation of allenic esters represented by the formula:

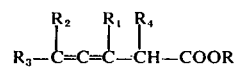

wherein $R_1$, $R_2$ and $R_4$ each represents hydrogen or a radical having from 1–20 carbon atoms; $R_3$ represents a radical having at least 2 carbon atoms; $R_2$ and $R_3$ may together form a cyclic ring; and R represents a radical having from 1–8 carbon atoms, said process comprising reacting a propargyl alcohol derivative represented by the following formula:

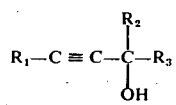

wherein $R_1$, $R_2$ and $R_3$ are as defined above with a 2-substituted ortho-acetic acid ester represented by the following formula:

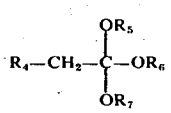

wherein $R_4$ is as defined above and $R_5$, $R_6$ and $R_7$, which may be the same or different, have the same meaning as R defined above, in the presence of an acidic catalyst.

2. A process for the preparation of allenic esters of claim 1 wherein said radical of said $R_1$, $R_2$ and $R_4$ has from 1–8 carbon atoms and wherein $R_3$ represents the group $R'-A_m-$, wherein $R'$ represents a radical of 5–30 carbon atoms of the formula

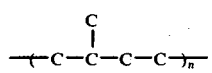

wherein $n$ is an integer of 1–6, –A– is an alkylene, alkenyl or alkynylene radical having 1–3 carbon atoms, and $m$ is an integer of 0–1, said process comprising reacting a propargyl alcohol derivative represented by the following formula:

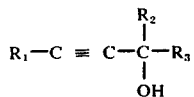

wherein $R_1$, $R_2$ and $R_3$ are as defined above, with a 2-substituted ortho-acetic ester represented by the following formula:

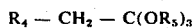

wherein $R_4$ is as defined above and $R_5$ has the same meaning as $R_1$ in the presence of an acidic catalyst.

3. The process of claim 1 wherein the acidic catalyst is an acid selected from the group consisting of carboxylic acids, sulfonic acids, mineral acids and Lewis acids.

4. The process of claim 25 wherein the acidic catalyst is a fatty acid having from 3 to 6 carbon atoms.

5. The process of claim 1 wherein the reaction is carried out at a temperature of 50° to 200°C.

6. A process for continuously preparing an $\alpha$, $\beta$, $\gamma$, $\delta$-unsaturated carboxylic acid ester comprising adding an alkali catalyst to the reaction product mixture of a propargyl alcohol derivative selected from the group consisting of 3,7-dimethyl-1-octyn-6-en-3-ol, 3,7,11-trimethyl-3,10-dodecadien-1-yn-3-ol, and 3,7,11,15-tetramethyl-6,10,14-hexadecatrien-1-yn-3-ol with a 2-substituted ortho-acetic acid ester represented by the following formula:

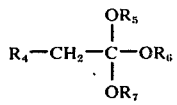

wherein $R_4$ is defined as in claim 1 and $R_5$, $R_6$ and $R_7$, which may be the same or different, have the same meaning as R in claim 1, without separating said allenic exter obtained therefrom and rearranging said allenic ester in the presence of said alkali catalysts to form said carboxylic acid ester.

7. The process of claim 6 wherein ester exchange is simultaneously conducted by conducting said rearrangement in the presence of an alcohol.

* * * * *